(12) United States Patent
Kwon et al.

(10) Patent No.: US 9,901,270 B2
(45) Date of Patent: Feb. 27, 2018

(54) BIOSIGNAL PROCESSING APPARATUS AND METHOD

(71) Applicant: Samsung Electronics Co., Ltd., Suwon-si (KR)

(72) Inventors: Ui Kun Kwon, Hwaseong-si (KR); Sang Joon Kim, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 197 days.

(21) Appl. No.: 14/718,630

(22) Filed: May 21, 2015

(65) Prior Publication Data

US 2016/0150987 A1    Jun. 2, 2016

(30) Foreign Application Priority Data

Nov. 27, 2014    (KR) .................. 10-2014-0167535

(51) Int. Cl.
*A61B 5/04* (2006.01)
*A61B 5/0488* (2006.01)
*A61B 5/00* (2006.01)

(52) U.S. Cl.
CPC ........ *A61B 5/04012* (2013.01); *A61B 5/0488* (2013.01); *A61B 5/681* (2013.01); *A61B 5/7207* (2013.01)

(58) Field of Classification Search
CPC ... A61B 5/04012; A61B 5/681; A61B 5/7207; A61B 5/0488
See application file for complete search history.

(56) References Cited

U.S. PATENT DOCUMENTS

| 8,447,704 B2 | 5/2013 | Tan et al. |
| 2011/0004072 A1* | 1/2011 | Fletcher ............... A61B 5/0002 600/300 |
| 2011/0213257 A1 | 9/2011 | Mahmood et al. |
| 2012/0316452 A1 | 12/2012 | Mahmood et al. |
| 2014/0128758 A1 | 5/2014 | Galloway et al. |
| 2015/0374258 A1* | 12/2015 | Peacock, III ...... G01R 33/4625 382/131 |

FOREIGN PATENT DOCUMENTS

| JP | 2009-509711 A | 3/2009 |
| KR | 10-0408498 B1 | 4/2004 |
| KR | 10-2006-0119472 A | 11/2006 |
| KR | 10-2012-0045526 A | 5/2012 |

* cited by examiner

*Primary Examiner* — Rex R Holmes
(74) *Attorney, Agent, or Firm* — NSIP Law

(57) ABSTRACT

A biosignal processing method involves estimating a baseline of a detected biosignal based on a comparison between the detected biosignal and a set value, and controlling a processing logic of the detected biosignal based on the estimated baseline.

19 Claims, 12 Drawing Sheets

500

501

BIOSIGNAL PROCESSING APPARATUS AND METHOD

CROSS-REFERENCE TO RELATED APPLICATION

This application claims the benefit under 35 USC 119(a) of Korean Patent Application No. 10-2014-0167535 filed on Nov. 27, 2014, in the Korean Intellectual Property Office, the entire disclosure of which is incorporated herein by reference for all purposes.

BACKGROUND

1. Field

The following description relates to an apparatus and method for biosignal processing.

2. Description of Related Art

A signal processing apparatus may filter a measured raw electromyogram (EMG) signal according to a desired frequency band in order to use a signal measured through an EMG sensor. The EMG signal may be an electrical potential or voltage, changing over time. The raw signal is an oscillating wave with an amplitude increase during muscle activation. The signal processing apparatus may use an absolute value of the filtered signal and a result value of a moving average (MAVG) in order to verify whether a desired EMG signal is present.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a biosignal processing apparatus includes a comparer configured to compare a detected biosignal to a set value, a baseline estimator configured to estimate a baseline of the detected biosignal based on an output value of the comparer, and a controller configured to control a processing logic of the detected biosignal based on the estimated baseline.

The controller may be configured to remove the estimated baseline from the detected biosignal.

The controller may be configured to increase, based on the processing logic, a threshold value to correspond to the estimated baseline.

The comparer may be configured to update the set value based on a comparison of the set value and a feature value obtained based on the detected biosignal.

The comparer may be configured to, in response to the feature value being greater than or equal to the set value, verify whether the feature value satisfies a predetermined reference and to adjust the set value based on a result of the verifying.

The general aspect of the apparatus may further include a motion artifact remover configured to remove a motion artifact associated with the detected biosignal.

The biosignal processing apparatus may include a wearable device.

The biosignal processing apparatus may be implemented as a system on chip, and the system on chip may be configured to be embedded in a wearable device.

In another general aspect, a biosignal processing apparatus may include a measurer configured to measure an electromyogram (EMG) signal, a comparer configured to compare the measured EMG signal to a set value, a baseline estimator configured to estimate a baseline of the measured EMG signal based on an output value of the comparer, and a controller configured to control a processing logic of the measured EMG signal based on the estimated baseline.

The controller may be configured to remove the estimated baseline from a detected EMG signal.

The controller may be configured to increase, based on the processing logic, a threshold value to correspond to the estimated baseline.

The comparer may be configured to update the set value based on a comparison of the set value and a feature value obtained based on the detected EMG signal.

The comparer may be configured to, in response to the feature value being greater than or equal to the set value, verify whether the feature value satisfies a predetermined reference and to adjust the set value based on a result of the verifying.

The general aspect of the apparatus may further include a motion artifact remover configured to remove a motion artifact associated with the detected biosignal.

The general aspect of the apparatus may further include an identifier configured to identify a gesture of a user based on the EMG signal processed based on the processing logic.

The biosignal processing apparatus may be a wearable device.

In another general aspect, a biosignal processing method involves estimating a baseline of the detected biosignal based on a comparison between a detected biosignal and a set value, and controlling a processing logic of the detected biosignal based on the estimated baseline.

The controlling may involve removing the estimated baseline from the detected biosignal.

The detected biosignal may include an electromyogram (EMG) signal.

In yet another general aspect, a non-transitory computer readable medium stores instructions that, when in execution, causes a computer to perform the biosignal processing method described above.

In yet another general aspect, a biosignal processing apparatus includes a processor configured to estimate a baseline of a detected EMG signal by comparing a set value with the EMG signal, and to process the EMG signal based on the estimated baseline.

The processor may be configured to estimate the baseline of the EMG signal by calculating a feature value of the EMG signal and comparing the feature value to the set value.

The processor may be configured to determine an occurrence of a physiological event by updating a threshold value for detecting the physiological event based on the estimated baseline.

The general aspect of the apparatus may further include an electrode configured to detect the EMG signal.

Other features and aspects will be apparent from the following detailed description, the drawings, and the claims.

BRIEF DESCRIPTION OF THE DRAWINGS

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

Figure 1:
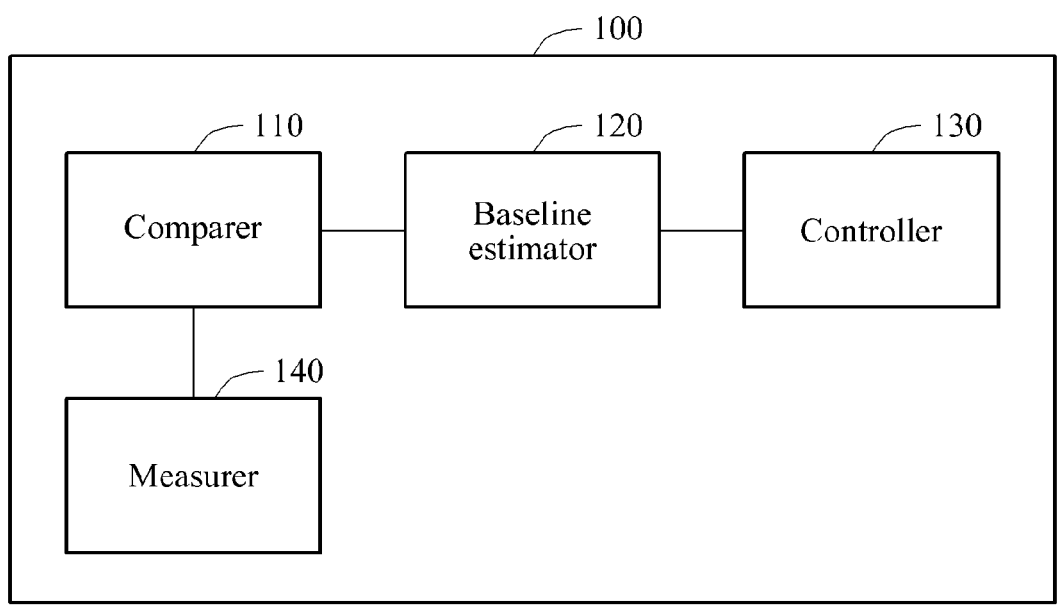
FIG. 1 is a diagram illustrating an example of a biosignal processing apparatus.

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Hereinafter, the examples will be described with reference to the accompanying drawings. Like reference numerals refer to like elements throughout.

Various alterations and modifications may be made to the examples. Here, the examples are not construed as limited to the disclosure and should be understood to include all changes, equivalents, and replacements within the idea and the technical scope of the disclosure.

The terminology used herein is for the purpose of describing particular examples only and is not to be limiting of the examples. As used herein, the singular forms "a", "an", and "the" are intended to include the plural forms as well, unless the context clearly indicates otherwise. It will be further understood that the terms "include/comprise" and/or "have" when used in this specification, specify the presence of stated features, integers, steps, operations, elements, components, and/or combinations thereof, but do not preclude the presence or addition of one or more other features, numbers, steps, operations, elements, components, and/or groups thereof.

Unless otherwise defined, all terms including technical and scientific terms used herein have the same meaning as commonly understood by one of ordinary skill in the art to which examples belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

When describing the examples with reference to the accompanying drawings, like reference numerals refer to like constituent elements and a repeated description related thereto will be omitted. When it is determined detailed description related to a related known function or configuration they may make the purpose of the examples unnecessarily ambiguous in describing the examples, the detailed description will be omitted here.

FIG. 1 illustrates a configuration of an example of a biosignal processing apparatus.

According to one example, a biosignal processing apparatus 100 may be provided as a standalone device that includes a sensor for detecting a biosignal and an input/out device such as an LCD screen that output the result of biosignal processing performed by the biosignal processing apparatus. According to another example, the biosignal processing apparatus 100 may be provided in form of a system on chip (SOC) and embedded in electronic devices, such as a wearable device or a mobile terminal.

Referring to FIG. 1, the biosignal processing apparatus 100 includes a comparer 110, a baseline estimator 120, and a controller 130. The comparer 110, the baseline estimator 120, and the controller 13 may include one or more processor and memory. In addition, the biosignal processing apparatus 100 includes a measurer 140. The measurer 140 may include a sensor, an electrode, or the like for measuring a biosignal.

The biosignal processing apparatus 100 may detect and process a biosignal. For example, the biosignal processing apparatus 100 may detect at least one of a bioimpedance, an electromyogram (EMG) signal, an electrocardiography (ECG) signal, and a photoplethysmogram (PPG). Although an example in which the measurement of the biosignal occurred within the biosignal processing apparatus 100 has been illustrated, in an alternative example, the biosignal processing apparatus may receive a biosignal from a separate device configured to detect a biosignal of a user. For example, the biosignal processing apparatus 100 may receive a biosignal such as an EMG signal, an ECG signal, and the like of the user, from the device via a communication interface. The communication interface may include a wireless internet interface, for example, a wireless local area network (WLAN), a wireless fidelity (Wi-Fi) direct, a digital living network alliance (DLNA), a wireless broadband (Wi-Bro), a world interoperability for microwave access (Wi-MAX), a high speed downlink packet access (HSDPA), and the like. The biosignal processing apparatus 100 may also include a local area communication interface, for example, a Bluetooth, a radio frequency identification (RFID), an infrared data association (IrDA), a ultra wideband (UWB), a Zigbee, a near field communication (NFC), and the like. Also, the communication interface may refer to as all interfaces, for example, a cable interface, performing external communication.

The biosignal processing apparatus 100 may amplify and preprocess the detected biosignal. For example, the biosignal processing apparatus 100 may increase a gain of the detected biosignal through an amplifier, for example, a differential amplifier and the like, and remove an artifact associated with the biosignal through the preprocessing.

Invasive EMG is accurate in sensing muscle activation, but is difficult to apply because it requires needle electrodes to be inserted through the skin and directly into the muscle fibers. In contrast, surface EMG only requires that conductive sensors be placed on the surface of the skin. However, surface EMG is fundamentally noisier than invasive EMG since motor unit action potentials must pass though body tissues such as fat and skin before they can be captured by a sensor on the surface. Due to the sensitivity of EMG sensors required to detect these signals, they also generally detect other electrical phenomena such as activity from other muscles, skin movement over muscles, and other environmental noise.

The biosignal processing apparatus 100 may include a motion artifact remover configured to remove a motion artifact associated with the detected biosignal. The motion artifact are introduced into the measured biosignal due to the movement of the user or due to physiological movements such as the expansion of the intercostal muscle due to breathing or the beating of the heart. The removal of the motion artifact facilitates the detection of signals that the user desires to detect from the measured raw biosignal. For example, a frequency spectrum of the EMG signal may appear in a range from zero through 500 hertz (Hz). When the motion artifact exists in the EMG signal, a frequency spectrum of the motion artifact may appear in a low frequency band, for example, a range from zero through 60 Hz or zero though 70 Hz. The motion artifact remover may remove the motion artifact associated with the biosignal through filtering. For example, the motion artifacts may be removed by removing signals in a range of zero to 70 Hz. However, the aforementioned frequency spectrum of the motion artifact is only an example and thus, the frequency spectrum of the motion artifact is not limited to the aforementioned example.

The biosignal processing apparatus 100 may post-process the biosignal from which the motion artifact is removed. The biosignal may include a sample having a negative value and a sample having a positive value. The biosignal processing apparatus 100 may apply an absolute value to the sample of the biosignal such that the sample having the negative value has the positive value. Also, the biosignal processing apparatus 100 may rectify the biosignal such that the biosignal has the positive value. The biosignal processing apparatus 100 may apply a moving average to the sample of the biosignal. The biosignal processing apparatus 100 may apply a root mean square (RMS) to the sample of the biosignal. The biosignal processing apparatus 100 may obtain a feature value, for example, a moving average and an RMS, of the sample through the post-processing. In addition, the biosignal processing apparatus 100 may smooth the biosignal through the post-processing.

The comparer 110 compares the detected biosignal to a set value. For example, the comparer 110 may compare the set value to a feature value obtained based on the biosignal. As described above, the feature value may include a moving average of the biosignal. The comparer 110 may update the set value based on a comparison of the set value and the feature value. For example, in response to the feature value being less than the set value, the comparer 110 may change the set value to the feature value. When the feature value is greater than or equal to the set value, the comparer 110 may increase the set value by adding a predetermined constant α to the set value. The comparer 110 may output the updated set value to the baseline estimator 120.

The baseline estimator 120 estimates a baseline of the biosignal based on an output value of the comparer 110. For example, the baseline estimator 120 may receive the updated set value from the comparer 110, and estimate the updated set value as the baseline of the biosignal. In one example, when a sample, for example, an $n^{th}$ sample, having a time index is input to the comparer 110, the comparer 110 may compare the set value to a feature value of the $n^{th}$ sample. The baseline estimator 120 may estimate the changed set value as a baseline of the $n^{th}$ sample. Also, when the set value of the $n^{th}$ sample is greater than or equal to the set value, the comparer 110 may increase the set value to correspond to the predetermined constant α, and output the increased set value to the baseline estimator 120. The baseline estimator 120 may estimate the increased set value as the baseline of the $n^{th}$ sample. When the baseline of the $n^{th}$ sample is estimated, an $(n+1)^{th}$ sample may be input to the comparer 110.

A baseline of the $(n+1)^{th}$ sample may be also estimated in the same way that the baseline of the $n^{th}$ sample is estimated. For example, a feature value of the $(n+1)^{th}$ sample may be compared to a set value. The set value compared to the feature value of the $(n+1)^{th}$ sample may be the baseline of the $n^{th}$ sample. The feature value of the $(n+1)^{th}$ sample may be compared to the baseline of the $n^{th}$ sample. In response to a determination that a result of the comparison represents that the feature value of the $(n+1)^{th}$ sample is less than the baseline of the $n^{th}$ sample, the baseline of the $(n+1)^{th}$ sample may be determined to be "the feature value of the $(n+1)^{th}$ sample". In response to a determination that the result of the comparison indicates that the feature value of the $(n+1)^{th}$ sample is greater than the baseline of $n^{th}$ sample, the baseline of the $(n+1)^{th}$ sample may be determined to be "the baseline of the $n^{th}$ sample+α".

In one example, it may be assumed that an envelope signal of a measured biosignal is a rectangular pulse. An envelope signal refers to a smooth curve outlining the extremes of a signal. In this hypothetically example, an amplitude of a valid signal that the user wants to detect may be relatively high in comparison to the measured biosignal in general, and the magnitude of the feature value of the valid signal may be determined to be greater according to a an increase in the amplitude of the valid signal relative to the remaining measured biosignal. In this example, a "valid signal" refers to a signal that a user desires to observe in a measured raw signal, and the valid signal may correspond to a signal of a rectangular portion of the rectangular pulse.

In another example, it may be assumed that the $(n+1)^{th}$ sample is a sample from which a valid signal starts. In this example, the $(n+1)^{th}$ sample may have a relatively greater feature value compared to the $n^{th}$ sample. When the $(n+1)^{th}$ sample is input to the comparer 110, the baseline of the $(n+1)^{th}$ sample may be estimated based on a result of comparing the feature value of the $(n+1)^{th}$ sample to the baseline of the $n^{th}$ sample. Since the feature value of the $(n+1)^{th}$ sample is greater than the baseline of the $n^{th}$ sample, the baseline of the $(n+1)^{th}$ sample may be "the baseline of the $n^{th}$ sample+α". Also, a feature value of an $(n+2)^{th}$ sample may be compared to the baseline of the $n^{th}$ sample. Since the feature value of the $(n+2)^{th}$ sample is greater than the baseline of the $n^{th}$ sample, a baseline of the $(n+2)^{th}$ sample may be presumed to be "the baseline of the $(n+1)^{th}$ sample+α". In the event that a plurality of samples that includes valid signals are consecutively input, the baseline of the sample may continuously increased each time a sample is input so as to reach α. When the baseline is increased in this manner, because the baseline may be removed from the biosignal to obtain the desired signal, the amplitude of the valid signal may be decreased as the time index increases.

For example, assuming that a $100^{th}$ sample has a feature value of "5", and $101^{st}$ through $200^{th}$ samples have a feature value of "50", valid signals may be the $101^{st}$ through $200^{th}$ samples. It is assumed that a baseline of the $100^{th}$ sample is "4". When the $101^{st}$ sample is input to the comparer 110, the comparer 110 may have an output value of "(4+α)", and a baseline of the $101^{st}$ sample may be "(4+α)". Since a baseline is removed from a feature value of the $101^{st}$ sample, the $101^{st}$ sample may have an amplitude of "50−(4+α)". A $102^{nd}$ sample may have an amplitude of "50−(4+2*α)", and a $200^{th}$ sample may have an amplitude of "50−(4+100*α)". When the feature value of the $101^{st}$ sample is compared to a feature value of the $200^{th}$ sample, amplitudes of valid signals may be decreased according to a signal processing due to a continuous increase in a baseline.

To prevent a decrease in an amplitude of a valid signal due to the signal processing in the above described situation, the comparer 110 may verify whether a feature value satisfies a predetermined standards in the event that a feature value of the biosignal is greater than or equal to a set value. Further, the comparer 110 may adaptively adjust the set value based on a result of the verifying. For example, the comparer 110 may verify whether a feature value represents a valid signal based on a threshold value set for detecting a valid signal. When a feature value of the input sample is greater than or equal to the threshold value, the comparer 110 may determine that the input sample is a valid signal.

The comparer 110 may adaptively adjust a set value based on a result of the verifying. For example, the comparer 110 may set α as "zero" based on the result of the verifying. In the event that α is set as "zero", a baseline of valid signal may be maintained. The comparer 110 may set α to have a smaller value based on the result of the verifying.

The controller 130 controls a processing logic of a biosignal based on a result of the estimating of the baseline. The processing logic may include a first logic (logic 1) in which a baseline is removed from a biosignal, and a second logic (logic 2) in which a predetermined threshold value is increased to correspond to a baseline. Hereinafter, further descriptions of the logics will be provided with reference to FIGS. 2A and 2B.

Figure 2A:
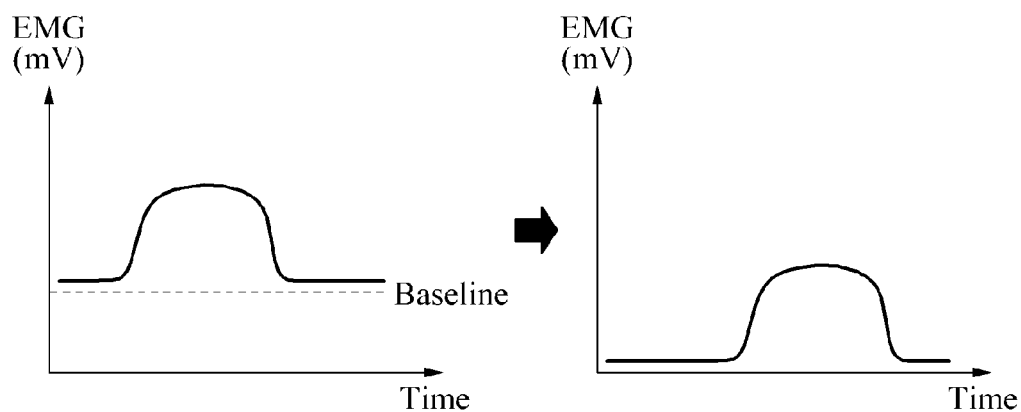
FIGS. 2A and 2B are diagrams illustrating examples of biosignal processing methods that use an estimated baseline.
Figure 2B:
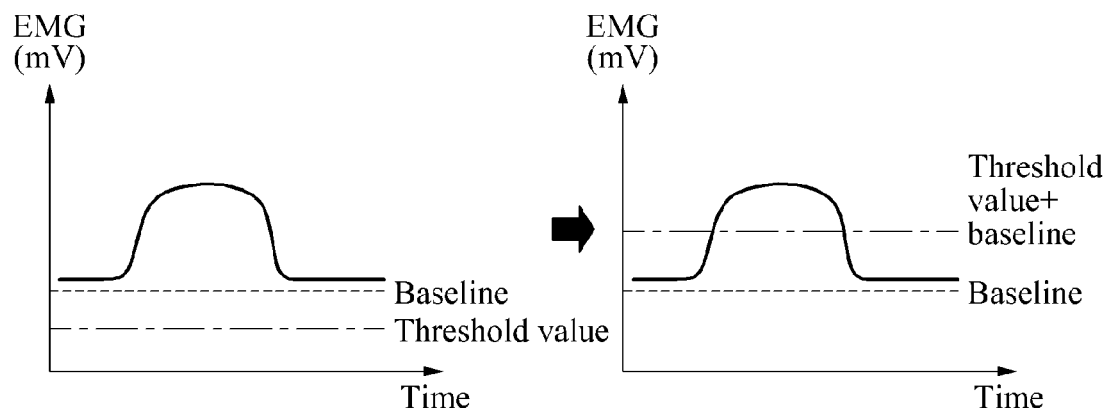

FIGS. 2A and 2B illustrate examples of a biosignal processing method using a baseline that may be performed by a biosignal processing apparatus.

FIG. 2A illustrates an example of a processing method in which a baseline is removed from a measured biosignal. The biosignal processing apparatus may estimate the baseline of the biosignal to be input. When the baseline is estimated, the biosignal processing apparatus may control the processing logic to the first logic (logic 1), and remove the baseline from the biosignal based on the first logic (logic 1).

FIG. 2B illustrates an example of a processing method in which a predetermined threshold value is increased to correspond to a baseline. The threshold value may be set in advance in order to verify whether an EMG signal generated by a contraction and relaxation of muscles is present. When the EMG signal is greater than or equal to the threshold value, the biosignal processing apparatus may determine that the EMG signal is present. Conversely, when the EMG signal is less than the threshold value, the biosignal processing apparatus may determine that the EMG signal is not present.

As illustrated in a left graph of FIG. 2B, a baseline of the EMG signal may be generated to be greater than the threshold value due to a change in a half cell potential or an impedance between an electrode and skin. When the baseline of the EMG signal is set to be greater than the threshold value, the biosignal processing apparatus may determine that the EMG signal is present at all times. The biosignal processing apparatus may not accurately detect the EMG signal. In this case, for example, the biosignal processing apparatus may determine that muscles of a user are moving even though the muscles of user are actually not moving.

The biosignal processing apparatus may estimate the baseline of the EMG signal and control its processing logic to the second logic (logic 2). As illustrated in a right graph of FIG. 2B, based on the second logic (logic 2), the biosignal processing apparatus may adjust the magnitude of a threshold value based on the estimated baseline. A new threshold value may be set based on a result of the estimating of the baseline of the EMG signal. Based on the setting of new threshold value, the biosignal processing apparatus may detect the occurrence of an EMG signal that a user desires to detect, such as the movement of a muscle group. Signals that does not reach the threshold value may be ignored.

Figure 3:
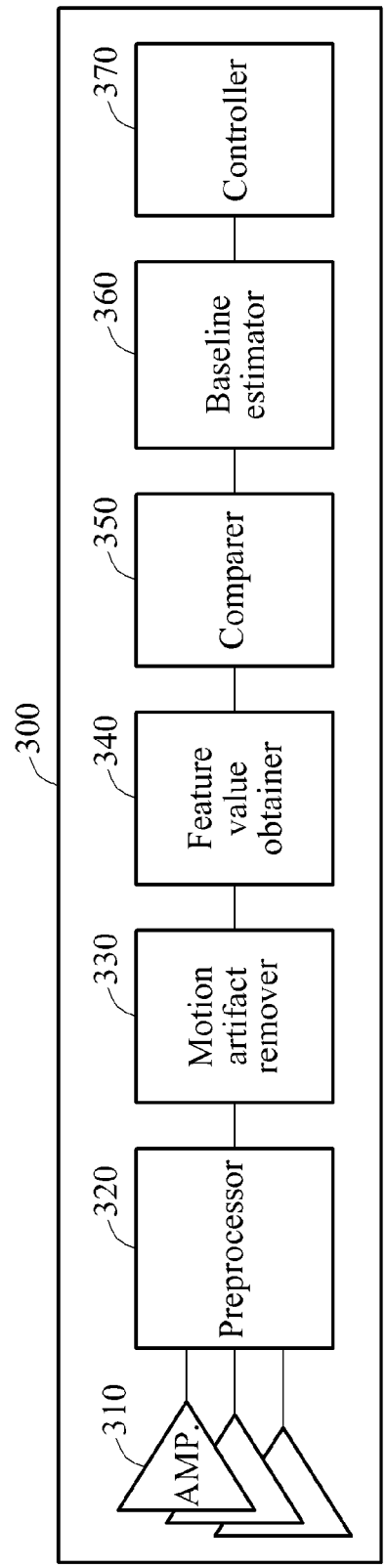
FIG. 3 is a diagram illustrating a configuration of an example of a biosignal processing apparatus for processing an electromyogram (EMG) signal.

FIG. 3 illustrates an example of a biosignal processing apparatus for processing an EMG signal.

A biosignal processing apparatus 300 may include a measurer (not shown). The measurer may include an electrode or other biosignal sensor. For example, the electrode may be a surface electrode. The surface electrode may be detachably attached to a body of a user or mounted on the body, and measure an electric signal generated by a contraction and relaxation of muscles of the user.

Referring to FIG. 3, the example of the biosignal processing apparatus 300 includes an amplifier 310. The amplifier 310 may amplify the measured EMG signal received from the measurer. A gain value of the EMG signal may be adjusted through the amplifier 310. The amplifier 310 may include a differential amplifier.

In this example, the biosignal processing apparatus 300 also includes a preprocessor 320. The preprocessor 320 may remove a noise included in the EMG signal through a filter.

The biosignal processing apparatus 300 may sample the EMG signal based on a sampling rate. For example, the biosignal processing apparatus 300 may sample the EMG signal based on the sampling rate of 1 kilohertz (kHz). A plurality of samples may be created based on the sampling.

The biosignal processing apparatus 300 includes a motion artifact remover 330. A frequency band of an EMG signal may be zero through 500 Hz, and a frequency band of a motion artifact may be a low frequency band, for example, zero through 60 Hz or zero through 70 Hz. The motion artifact remover 330 may remove a motion artifact by filtering.

The biosignal processing apparatus 300 includes a feature value obtainer 340. An EMG signal may include a sample having a negative amplitude. The feature value obtainer 340 may apply an absolute value to the sample such that the sample having the negative value has a positive amplitude. In addition, the feature value obtainer 340 may obtain a moving average of a sample. The feature value obtainer 340 may obtain a feature value of a sample using Equation 1.

$$MAV = \frac{1}{N}\sum_{k=1}^{N} |x(k)| \quad \text{[Equation 1]}$$

In Equation 1, MAV corresponds to a moving average of a sample, N corresponds to a number of samples, x(k) corresponds to a sample, and k corresponds to an index of a sample. The aforementioned feature value is only an example, a feature value of a sample is not limited to the foregoing.

The biosignal processing apparatus 300 includes a comparer 350. The comparer 350 may compare an EMG signal to a set value. The comparer 350 may compare a set value to the input feature value of sample. The biosignal processing apparatus 300 also includes a baseline estimator 360 configured to estimate a baseline of the EMG signal based on an output value of the estimator 350, and a controller 370. Hereinafter, a further description will be provided with reference to FIG. 4. The amplifier 310 may include an electrical circuit, a processor and/or a memory. The preprocessor 320, motion artifact remover, feature value obtainer 340, comparer 350, baseline estimator 360, and controller 370 may include one or more processor and/or memory.

Figure 4:
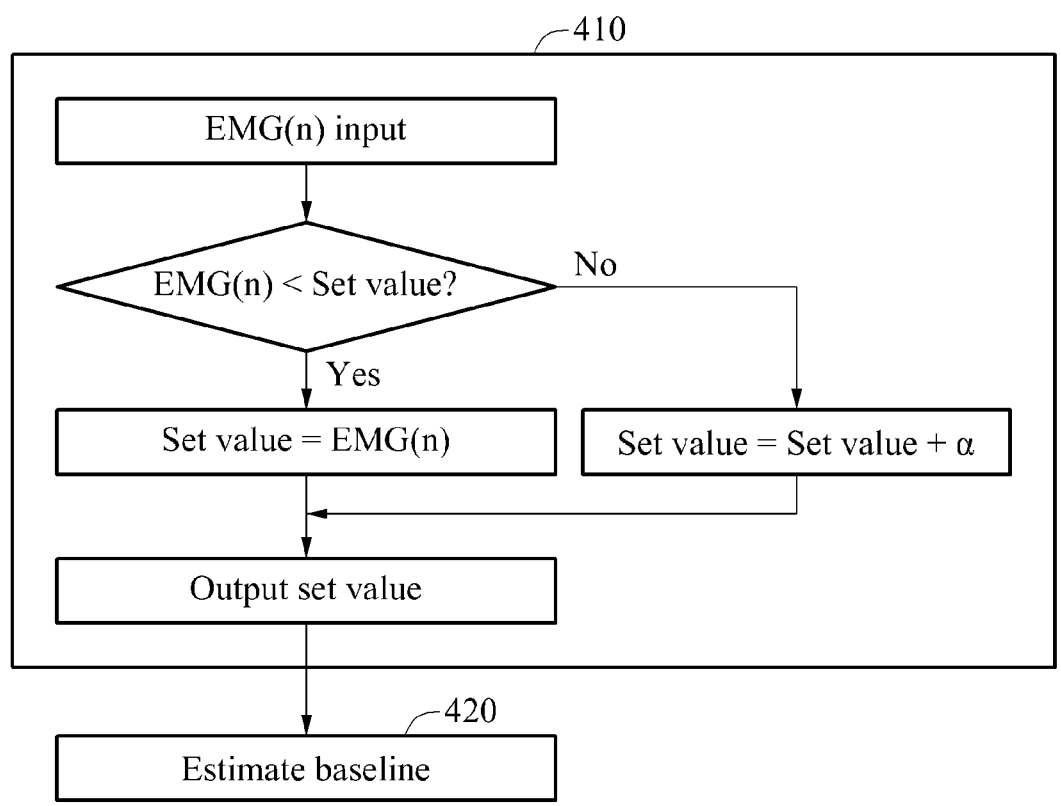
FIG. 4 is a flowchart illustrating an example of a method for estimating a baseline.

FIG. 4 illustrates an example of a method for estimating a baseline.

Referring to FIG. 4, a comparer 410 may receive an input of a first EMG measurement (EMG 1) as a first sample. The comparer 410 may compare a set value to a feature value of the first EMG measurement (EMG 1). In this example, the set value may be initially set to a value considerably greater than the feature value of the EMG 1. Since the feature value of the first sample is less than the set value, the comparer 410 may later change the set value to the feature value of the EMG 1. The feature value of the EMG 1 may be estimated as a baseline of the EMG 1.

As time elapses, the comparer 410 may receive an input of an EMG (n), which is the (n)-th EMG measurement. The comparer 410 may compare a set value to a feature value of the EMG (n). The comparer 410 may update the set value based on a comparison of the set value and the feature value of the EMG (n). Concisely, when the feature value of the EMG (n) is less than the set value, the comparer 410 may change the set value to the feature value of the EMG (n). When the feature value of the EMG (n) is greater than or equal to a set value, the comparer 410 may add a predetermined constant α to the set value. When the feature value of the EMG (n) is greater than or equal to the set value, the comparer 410 may change the set value to a set value+α. Whenever a sample is input, a set value may be updated. The comparer 410 may output the updated set value to a baseline estimator 420.

The baseline estimator 420 may estimate a baseline of an EMG signal based on an output value of the comparer 410. The baseline of the EMG (n) may be a feature value of the EMG(n) or a feature value+α.

In an example, when the feature value of the EMG (n) is greater than or equal to the set value, the comparer 410 may verify whether the feature value of the EMG (n) satisfies a predetermined reference. The comparer 410 may adaptively adjust the set value based on a result of the verifying.

In a case that the EMG (n) includes signals resulting from the movement of a muscle, feature values of samples included in certain sample intervals may be greater than feature values of samples outside the sample intervals. The certain sample intervals with large feature values may correspond to intervals during which an electric signal generated by a contraction and a relaxation of muscles of the user is detected. Baselines of samples prior to the sample intervals with large feature values may be estimated to be less than the feature values of samples included in the sample intervals. In this case, since the feature values of samples included in the sample intervals are greater than the set value, the comparer 410 may output as a set value+α. Due to the set value be set to +α, the baselines of samples included in the above described sample intervals may be increased. As a result, a baseline removed from an amplitude of a first sample of the predetermined sample interval and a baseline removed from an amplitude of a last sample of the predetermined sample interval may be different. Due to a continuous increase of a baseline, the baseline removed from the amplitude of the last sample of the predetermined sample interval may be greater than the baseline removed from the amplitude of first sample on the predetermined sample interval. In such an event, an amplitude of the processed signals from the sample interval may be decreased due to an increase in a sample index, and a compensating mechanism may become necessary for correct detection of the signal.

The comparer 410 may verify whether the EMG (n) is a sample that corresponds to an electric signal generated by activities of muscles of a user. For example, the comparer 410 may use a predetermined threshold value in order to verify whether the EMG (n) corresponds to an electric signal generated by a contraction of muscles of a user. When a feature value of the EMG (n) is greater than or equal to a threshold value, the comparer 410 may verify that the EMG (n) corresponds to the electric signal generated by the contraction of muscles of the user.

The comparer 410 may adaptively adjust α based on a result of the verifying. For example, the comparer 410 may reset α as "zero". In addition, the comparer 410 may reset α to be a smaller value. In this example, α may be reset, thereby preventing the distortion of a signal that the user desires to observe.

Referring back to FIG. 3, a controller 370 may control a processing logic that is applied to an EMG signal based on the estimated baseline. The processing logic of the EMG signal may include a first logic (logic 1) in which a baseline is removed from an EMG signal and a second logic (logic 2) in which a predetermined threshold value is increased to correspond to a baseline.

When a baseline is estimated, a controller 370 may remove the baseline from an EMG signal. For example, when a baseline is estimate from an EMG (n) or the current EMG measurement, a magnitude of the baseline may be reduced in a feature value of the EMG (n).

In an example, when a baseline is estimated, the controller 370 may add a baseline to a predetermined threshold value. A threshold value may be set in order to detect a desired signal corresponding to an electric signal generated by a contraction and relaxation of muscles of a user, of a measured signal. A magnitude of the measured signal being less than the threshold value may indicate that the desired signal is not detected. A magnitude of the measured signal being greater than or equal to the threshold value may indicate that the desired signal is detected.

A baseline of an EMG signal may be greater than a threshold value due to a change in a half cell potential or an impedance between an electrode and skin. The controller 370 may not detect a desired signal through the threshold value. The controller 370 may verify whether the estimated baseline is greater than or equal to the threshold value, and may increase a predetermined threshold value to correspond to a size of a baseline based on a result of the verifying.

Although not illustrated in FIG. 3, the biosignal processing apparatus 300 may include an identifier configured to identify a gesture of a user based on an EMG signal processed based on the processing logic.

The gesture of user may refer to as a motion of a user, for example, clenching fists and the like. The gesture may correspond to a contraction and relaxation of predetermined muscles. The gesture of user may be identified based on a detection of an electric signal generated by the contraction and relaxation of the predetermined muscles.

For example, it is assumed that the biosignal processing apparatus 300 is placed on a wrist of a user. When the user performs a gesture of lowering a hand from top to bottom, the biosignal processing apparatus 300 may verify a gesture of which a user makes as a gesture of lowering a hand from top to bottom using an EMG signal detected based on a contraction and relaxation of wrist muscles.

The aforementioned descriptions of FIGS. 1 through 2B may be also applicable to the descriptions of FIG. 3.

Figure 5A:
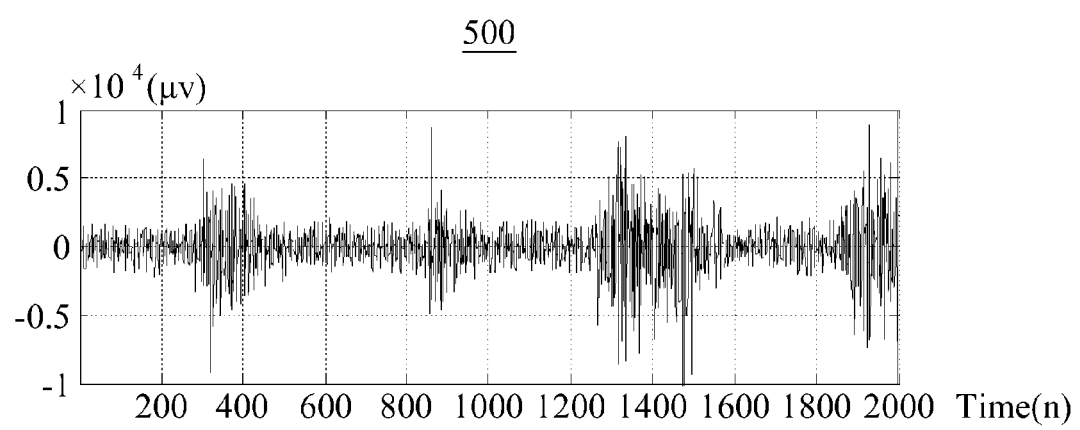
FIGS. 5A and 5B are graphs illustrating examples of EMG signal waveforms corresponding to a motion artifact.
Figure 5A:
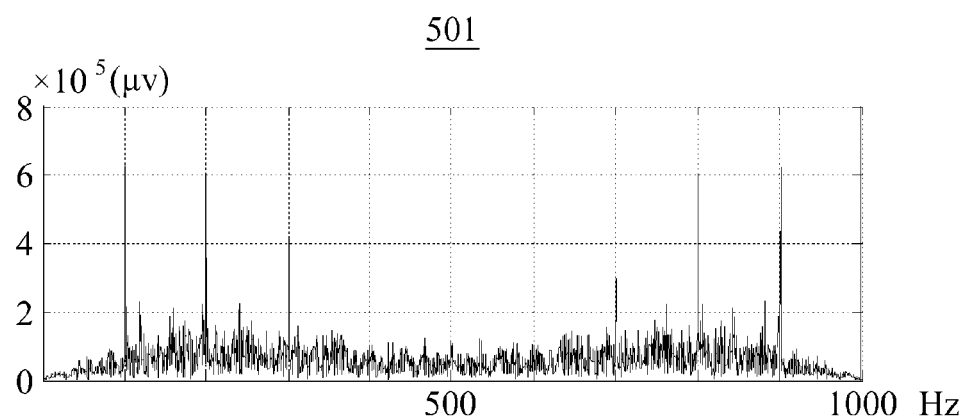
Figure 5B:
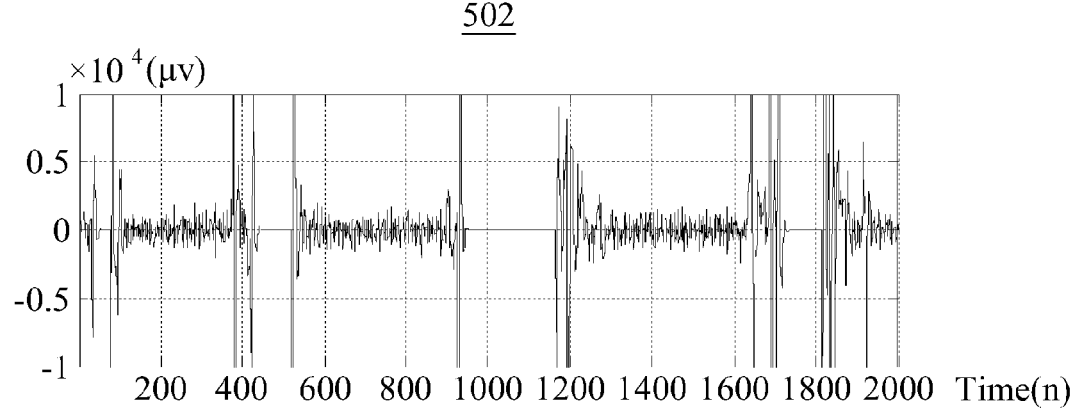
Figure 5B:
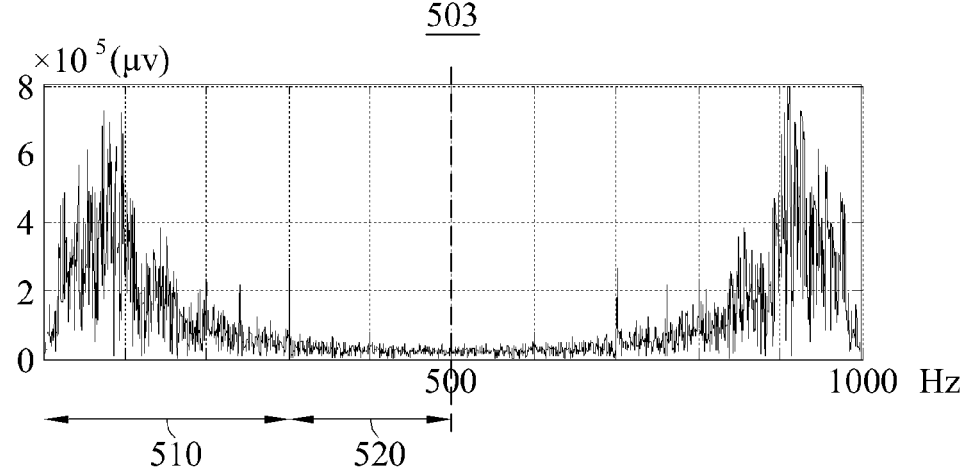

FIGS. 5A and 5B illustrate examples of EMG signals including a motion artifact.

FIG. 5A illustrates examples of EMG signals 500 and 501 measured through a dry electrode. A first signal 500 illustrated in FIG. 5A is a signal of a time area. In general, a biosignal measured through a dry electrode includes more noise than of a biosignal measured through a wet electrode. A second signal 501 in FIG. 5A is a signal in which the first signal 500 is converted into a frequency band. A measured EMG signal may have a frequency band of zero through 500 Hz. The EMG signal converted into the frequency band may be flat throughout the entire frequency band.

FIG. 5B illustrates additional examples of EMG signals 502 and 503 including motion artifacts. A first signal 502 in FIG. 5B is a signal of a time area. In the first signal 502, an interval during which a signal is stopped can be detected. The interval during which the signal is stopped may be an interval at which a motion artifact is generated. Measuring a biosignal through a dry electrode may be vulnerable to a motion artifact. A signal at which the first signal 502 is converted into a frequency band is illustrated as a second signal 503 in FIG. 5B.

Referring to the second signal 503 illustrated in FIG. 5B, a low frequency spectrum of a motion artifact may be formed in a low frequency band 510, for example, zero through 60 Hz or zero through 70 Hz. A frequency band of a desired signal of an EMG signal is indicated as a frequency band 520. As described, the desired signal may correspond to an electric signal generated by activities of muscles. A biosignal processing apparatus may filter the measured EMG signal to remove a motion artifact.

Signal frequencies of the frequency band illustrated in FIGS. 5A and 5B are provided only as examples; the frequency band of motion artifact, the frequency band of desired signal, and the frequency band of EMG signal are not limited to the aforementioned examples.

FIGS. 6A through 7C illustrate examples of an EMG signal to be processed.

The EMG signal may be measured through multiple channels. For example, the EMG signal may be measured through three channels.

Figure 6A:
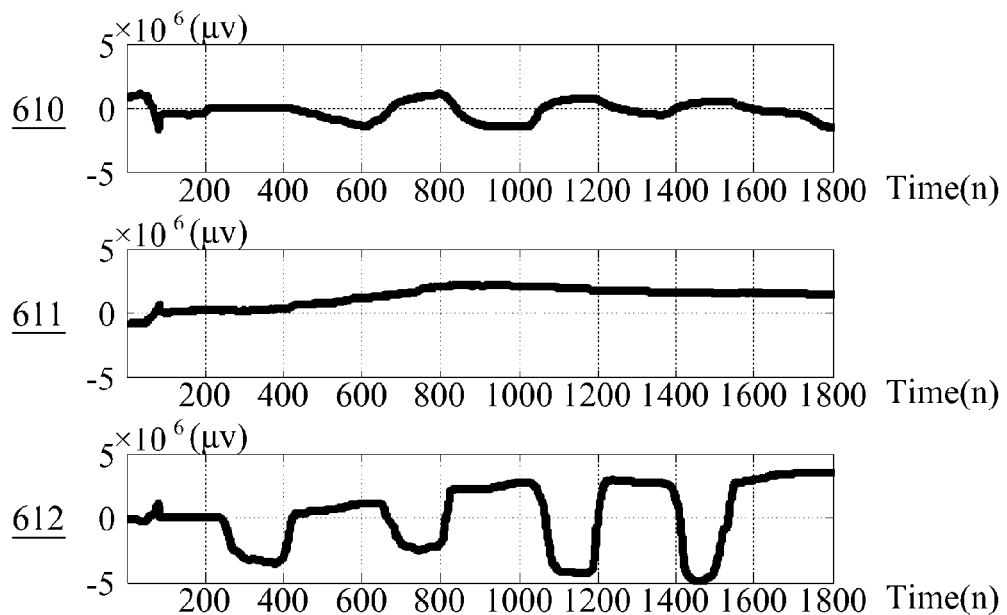
FIGS. 6A through 7C are graphs illustrating examples of EMG signals that are processed.

FIG. 6A illustrates EMG signals 610, 611 and 612 of which gains are obtained through an amplifier or EMG signals measured through the three channels. For example, a differential amplifier may be used to amplify an EMG signal.

Figure 6B:
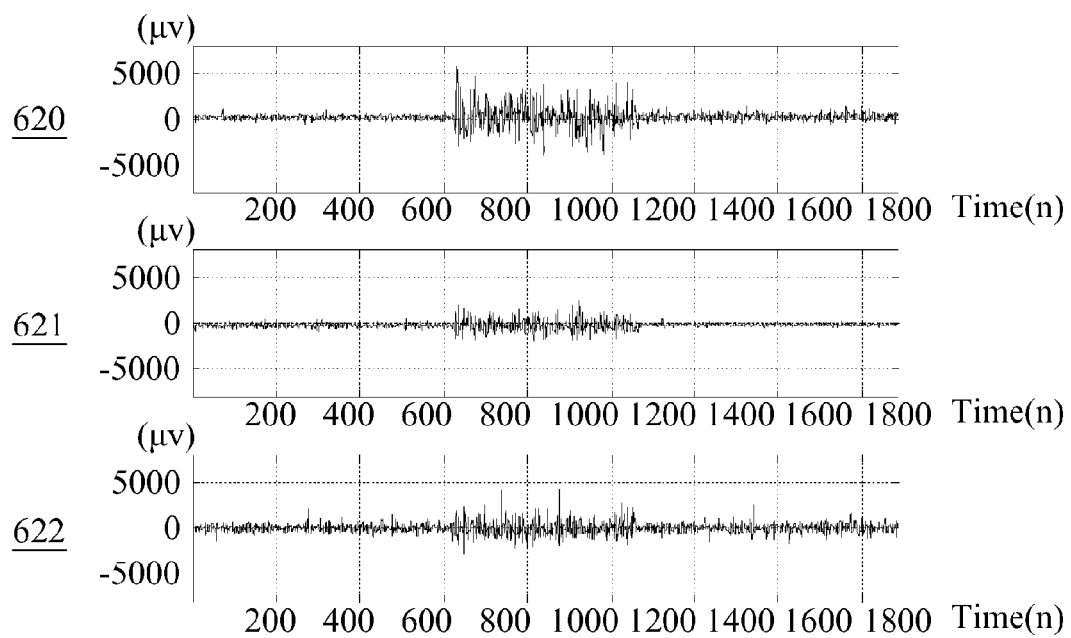

FIG. 6B illustrates that the EMG signals 610, 611 and 612 are preprocessed respectively, and EMG signals 620, 621 and 622 are obtained respectively when each of motion artifacts of EMG signals 610, 611 and 612 are removed. Noise occurring due to an interface between an electrode and skin may be removed through preprocessing. A motion artifact included in the preprocessed EMG signals may be removed by filtering of the preprocessed EMG signals.

Figure 6C:
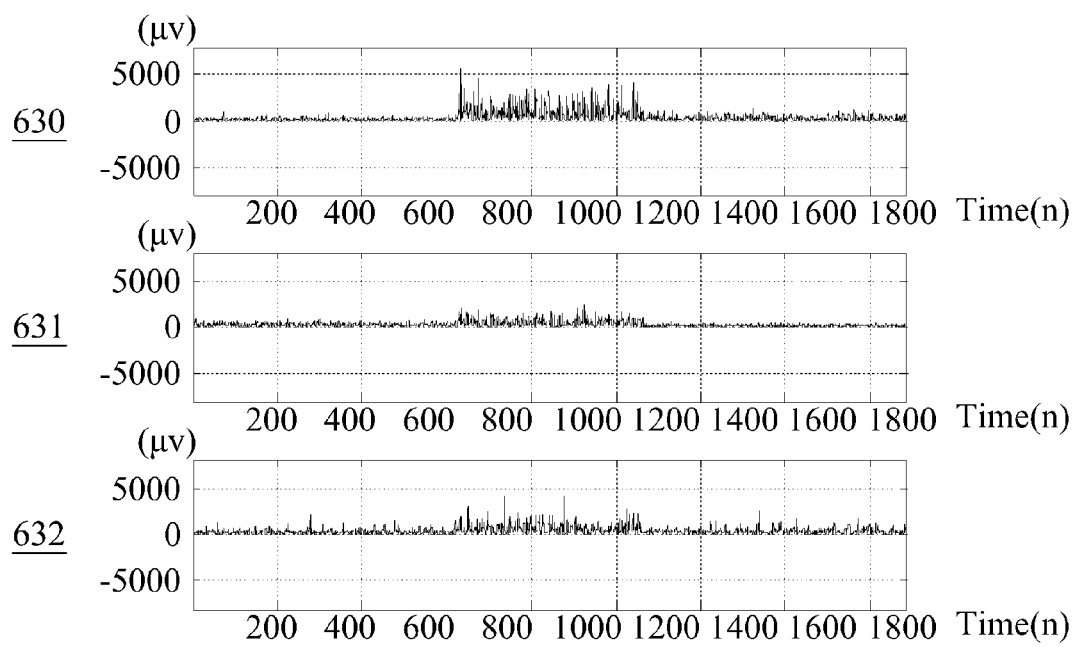

FIG. 6C illustrates EMG signals 630, 631 and 632 that are obtained when absolute values are applied to the EMG signals 620, 621, and 622, respectively. In FIGS. 6A and 6B, some of samples have negative amplitude values. In FIG. 6C, each sample has respective positive amplitude values.

Figure 7A:
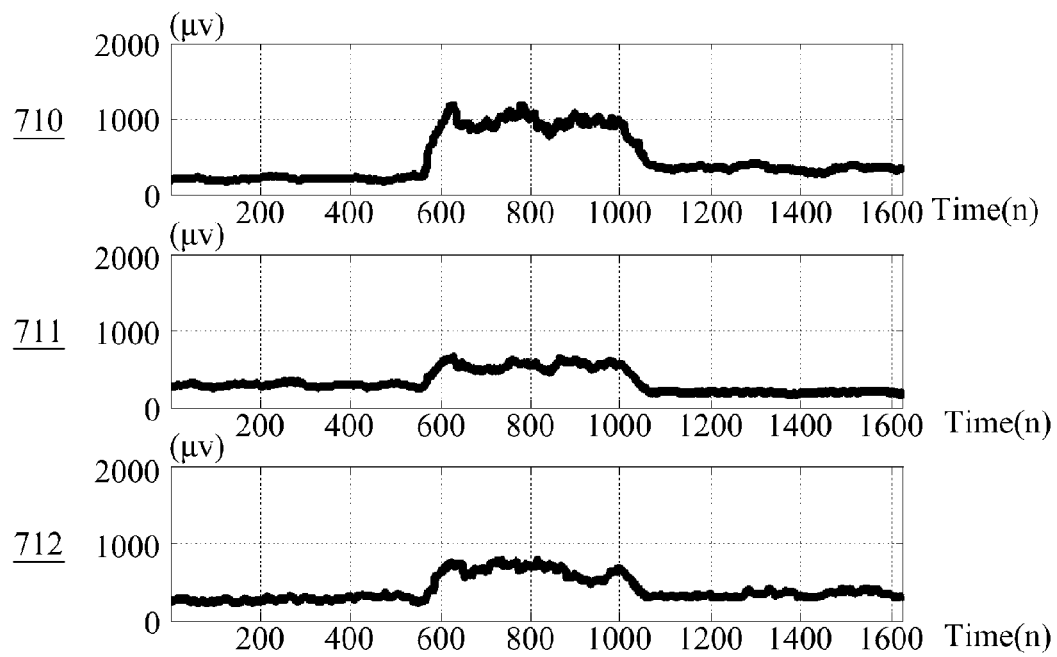

FIG. 7A illustrates that EMG signals 710, 711 and 712 are obtained when moving averages are applied to the EMG signals 630, 631, and 632, respectively. An absolute value and a moving average are applied to a sample, thereby obtaining a feature value of the sample. Referring to FIG. 7A, amplitudes of samples of which a time index n is 600 through 1000 are higher than other samples. The samples of which the time index n is 600 through 1000 may correspond to electric signals generated by activities of muscles. The samples of which the time index n is 600 through 1000 may be signals a user desires to observe among EMG signals.

Referring to FIG. 7A, a baseline may be created throughout the entire samples. Each magnitude of baselines created for each channel may be different from each other.

Figure 7B:
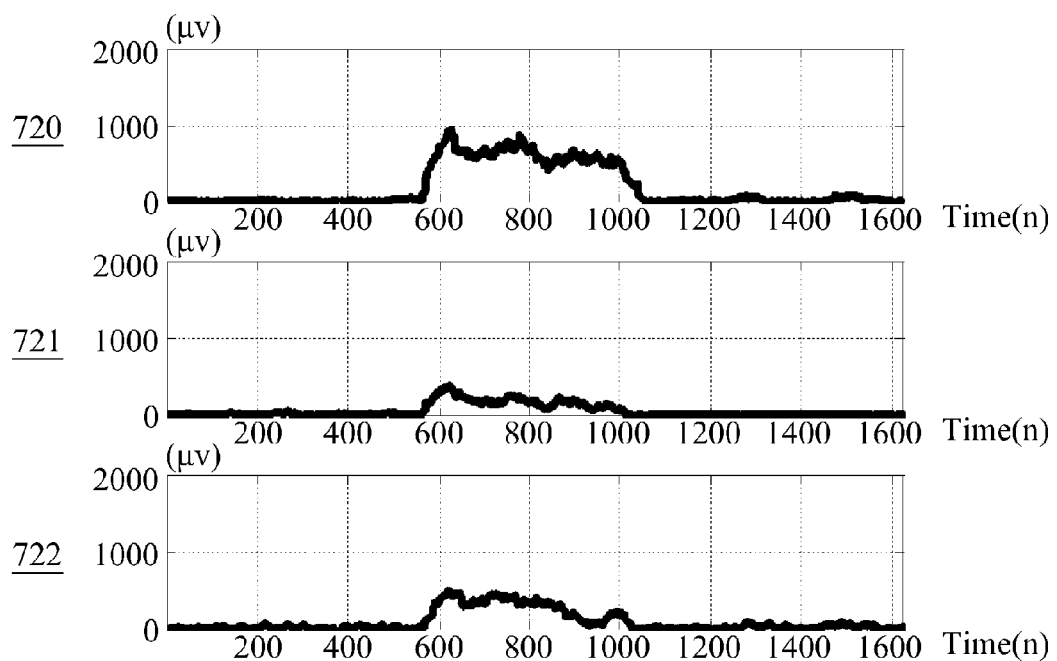

FIG. 7B illustrates EMG signals 720, 721, and 722 of which baselines are removed. When the baselines are removed, a desired signal may be easily detected from the measured EMG signals. Referring to FIG. 7A, the amplitudes of samples of which the time index n is 600 through 1000 may be substantially identical. Referring to FIG. 7B, at an interval during which the time index n ranges between 600 and 1000, the greater the time index n, the amplitudes of the samples is lower. At the interval during which the time index n is 600 through 1000, the greater the time index n, the greater the sizes of the estimated baselines. As described, since $\alpha$ is added to a feature value, the greater the time index n, the bigger the sizes of the baselines. At the interval at which the time index n is 600 through 1000, the greater the time index n, the bigger the sizes of removed baselines. Accordingly, the greater the time index n, the lower the amplitudes of the samples.

Figure 7C:
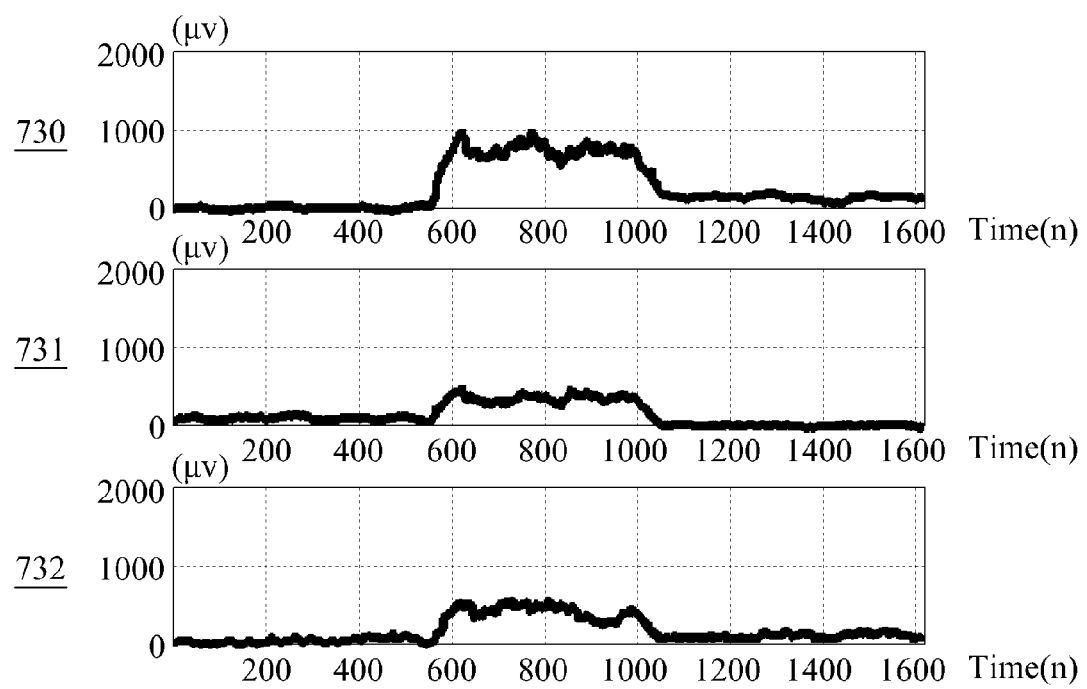

FIG. 7C illustrates signals 730, 731 and 732 of which $\alpha$ is reset. The biosignal processing apparatus may verify whether a feature value of a sample is greater than a threshold value. When the feature value is greater than or equal to the threshold value, $\alpha$ is reset as "zero" or $\alpha$ is reset by adaptively adjusting $\alpha$. As described with reference to FIG. 7B, when $\alpha$ is not reset, a magnitude of a desired signal may be decreased to correspond to an increased a time index n. Based on circumstances, when $\alpha$ is not reset, the magnitude of the desired signal may be "zero". Referring to FIG. 7C, when $\alpha$ is reset, an amplitude of the desired signal may not be decreased to correspond to an increased the time index n. Here, the amplitude of the desired signal may be almost regular. Based on the reset of $\alpha$, only baselines may be removed from the measured EMG signals through a plurality of channels, in lieu of distorting a desired signal. An application using the desired signal may be more accurately executed.

The aforementioned descriptions of FIGS. 5A through 7C may be also applicable to the descriptions of FIGS. 1 through 4.

Figure 8A:
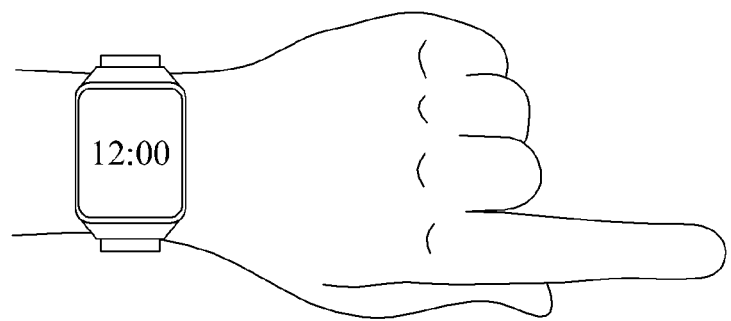
FIGS. 8A and 8B are illustrations of an example of a wearable device that includes a biosignal processing apparatus.
Figure 8B:
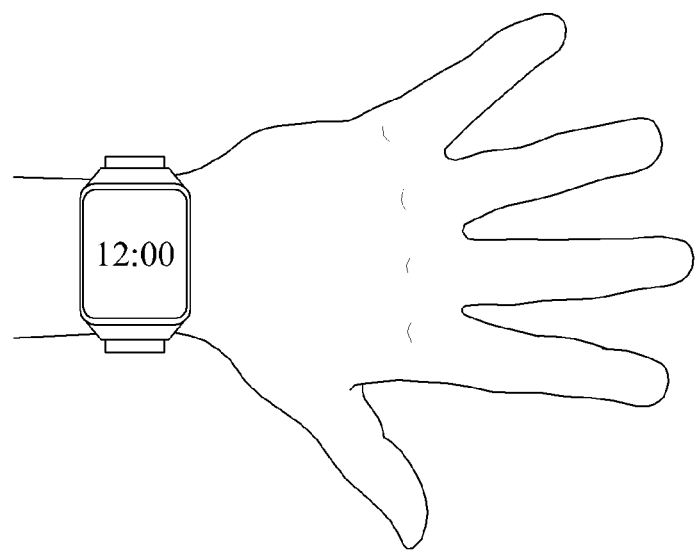

FIGS. 8A and 8B illustrate examples of a wearable device including a biosignal processing apparatus.

The biosignal processing apparatus may be implemented and provided in the wearable device. In this example, the wearable device is a watch that includes a display screen, a housing in which electronic components and an electrode are located, and a wristband for placing the housing over a waist of a user; however, the implementation is not limited thereto. For instance, in another example, the biosignal processing apparatus may be implemented as a belt, an arm band, a portable electronic terminal, a medical device, and the like. The wearable device illustrated in FIG. 8A may measure an EMG signal of a user by using an electrode located at a lower side of the housing or the wristband, and may identify a gesture performed by a user based on the EMG signal. A gesture illustrated in FIG. 8A is a gesture of a user stretching an index finger out of a clenched fist. When the user clenching the fist stretches the index finger, the wearable device may detect activation of muscles used for stretching the index finger. The wearable device may measure an electric signal generated by activation of the muscles. The wearable device may analyze the measured electric signal, and identify a type of gesture of which a user makes based on a result of the analyzing. The gesture of the user stretching the index finger out of a clenched fist may correspond to an input to initiate a function of the wearable device. When the gesture is identified, the wearable device may implement a predetermined function since the input is performed to implement the function. Referring to FIG. 8B, a gesture of a user stretching all fingers is illustrated. The wearable device may detect an EMG signal of muscles used for stretching all the fingers, and identify a gesture of which a user is making based on a result of the detecting.

While an example in which a hand gesture of the user is detected is illustrated in FIGS. 8A and 8B, the present disclosure is not limited thereto. In another example, various other physiological events such as walking, talking, exercising, moving of the arm, and the like, may be detected.

Figure 9:
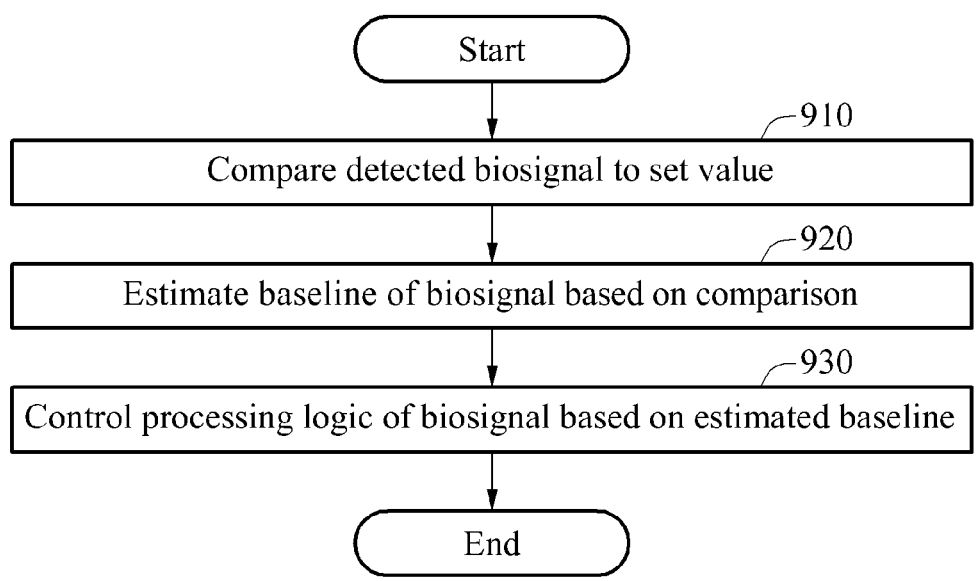
FIG. 9 is a flowchart illustrating an example of a biosignal processing method.

FIG. 9 illustrates an example of a biosignal processing method. The biosignal processing method may be performed by a biosignal processing apparatus.

The biosignal processing apparatus may detect a biosignal through a surface electrode, for example, a dry electrode. Also, the biosignal processing apparatus may receive a biosignal detected by a device connected to the biosignal processing apparatus. The biosignal processing apparatus may compare, at a processor, a set value to the received biosignal. The detected biosignal may be at least one of a bioimpedance, an EMG signal, an ECG signal, and a PPG.

The biosignal processing apparatus may preprocess, at the processor, the detected biosignal, and remove a motion artifact associated with the detected biosignal. Also, the biosignal processing apparatus may sample the detected biosignal, and divert the detected biosignal into a digital signal.

In operation 910, the biosignal processing apparatus compares the detected biosignal to the set value.

In operation 920, using the processor, the biosignal processing apparatus estimates a baseline of the detected biosignal based on the comparison of the set value and the biosignal.

In operation 930, using the processor, the biosignal processing apparatus may control a processing logic of the detected biosignal based on the estimated baseline. The processing logic of the biosignal may include a first logic (logic 1) in which a baseline is removed from a biosignal, and a second logic (logic 2) in which a predetermined threshold value is increased to correspond to a baseline The biosignal processing apparatus may remove the baseline from the biosignal. For example, the biosignal processing apparatus may subtract a size of a baseline from a feature value of an $n^{th}$ sample. The biosignal processing apparatus may add the size of a baseline to a set threshold value for detecting the biosignal. The threshold value may be reset based on the estimated baseline.

Since the aforementioned descriptions of FIGS. 1 through 8B are applicable to the descriptions of FIG. 9, repeated descriptions will be omitted for conciseness.

The apparatuses, units, modules, devices, and other components illustrated in FIGS. 1 and 3 that perform the operations described herein with respect to FIGS. 2, 4, 5A-7C and 9 are implemented by hardware components. Examples of hardware components include controllers, sensors, generators, drivers, and any other electronic components known to one of ordinary skill in the art. In one example, the hardware components are implemented by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIGS. 2, 4, 5A-7C and 9. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD- RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A biosignal processing apparatus comprising:
   a comparer configured to
      compare a feature value of a detected biosignal to a set value,
      determine a determination result indicating whether the feature value is less than the set value, and
      update the set value based on the determination result;
   a baseline estimator configured to estimate a baseline of the detected biosignal based on the updated set value; and
   a controller configured to control a processing logic of the detected biosignal based on the estimated baseline.

2. The apparatus of claim 1, wherein the controller is configured to remove the estimated baseline from the detected biosignal.

3. The apparatus of claim 1, wherein the controller is configured to increase, based on the processing logic, a threshold value based on the estimated baseline.

4. The apparatus of claim 1, further comprising:
   a motion artifact remover configured to remove a motion artifact associated with the detected biosignal.

5. The apparatus of claim 1, wherein the biosignal processing apparatus comprises a wearable device.

6. The apparatus of claim 1, wherein the biosignal processing apparatus is implemented as a system on chip, and the system on chip is configured to be embedded in a wearable device.

7. A biosignal processing method comprising:
   comparing a feature value of a detected biosignal to a set value;
   determining a determination result indicating whether the feature value is less than the set value;
   updating the set value based on the determination result;
   estimating a baseline of the detected biosignal based on the updated set value; and
   controlling a processing logic of the detected biosignal based on the estimated baseline.

8. The method of claim 7, wherein the controlling comprises removing the estimated baseline from the detected biosignal.

9. The method of claim 7, wherein the detected biosignal comprises an electromyogram (EMG) signal.

10. A non-transitory computer readable medium storing instructions that, when in execution, causes a computer to perform the method of claim 7.

11. The apparatus of claim 1, wherein the comparer is configured to:
    upon the determination result indicating that the feature value is less than the set value, update the set value by setting the set value equal to the feature value; and
    upon the determination result indicating that the feature value is not less than the set value, update the set value the set value.

12. The apparatus of claim 11, wherein the comparer is further configured to, upon the determination result indicating that the feature value is not less than the set value, determine a validity result indicating whether the feature value is greater than or equal to a validity threshold value.

13. The apparatus of claim 12, wherein the comparer is further configured to adjust the increment value based on the validity result.

14. The apparatus of claim 13, wherein the comparer is further configured to, upon the validity result indicating that the feature value is not greater than or equal to the validity threshold value, set the increment value to 0.

15. The apparatus of claim 1, further comprising a measurer configured to detect the biosignal.

16. The apparatus of claim 15, wherein the measurer comprises a surface electrode.

17. The apparatus of claim 3, wherein the controller is further configured to determine an occurrence of a physiological event in the detected biosignal based on the threshold value.

18. The apparatus of claim 17, further comprising an identifier configured to identify a gesture of a user based on the occurrence of the physiological event.

19. The apparatus of claim 1, wherein the baseline estimator is configured to estimate the baseline by setting the baseline to be equal to the updated set value.

* * * * *